US00PP34068P3

(12) United States Plant Patent
Neumüller

(10) Patent No.: US PP34,068 P3
(45) Date of Patent: Mar. 29, 2022

(54) ***PRUNUS* ROOTSTOCK TREE NAMED 'DHPRS2'**

(50) Latin Name: ***Prunus domestica* x *Prunus spinosa***
Varietal Denomination: Dhprs2

(71) Applicant: Michael Neumüller, Hallbergmoos (DE)

(72) Inventor: Michael Neumüller, Hallbergmoos (DE)

(73) Assignee: Michael Neumüller, Hallbergmoos (DE)

( * ) Notice: Subject to any disclaimer, the term of this patent is extended or adjusted under 35 U.S.C. 154(b) by 0 days.

(21) Appl. No.: 17/024,945

(22) Filed: Sep. 18, 2020

(65) Prior Publication Data

US 2021/0084860 A1 Mar. 25, 2021

Related U.S. Application Data

(60) Provisional application No. 62/973,196, filed on Sep. 20, 2019.

(51) Int. Cl.
*A01H 5/06* (2018.01)
*A01H 6/74* (2018.01)
*A01H 5/08* (2018.01)

(52) U.S. Cl.
USPC ..... Plt./180
CPC ..... *A01H 6/7427* (2018.05); *A01H 5/06* (2013.01); *A01H 5/08* (2013.01)

(58) Field of Classification Search
USPC ..... Plt./180
CPC ..... A01H 6/7427; A01H 5/06
See application file for complete search history.

(56) References Cited

U.S. PATENT DOCUMENTS

PP28,440 P3 * 9/2017 Neumuller ..... A01H 6/7427 Plt./180

OTHER PUBLICATIONS

UPOV hit on *Prunus* rootstock plant named, 'DHPRS2', QZ PBR 20192204, filed Sep. 9, 2019.*
CPVO application for prunus rootstock named, 'Dhprs2', application No. 20192204, filed Sep. 9, 2019.*

* cited by examiner

*Primary Examiner* — Anne Marie Grunberg
(74) *Attorney, Agent, or Firm* — The Webb Law Firm

(57) ABSTRACT

A new and distinct variety of *Prunus* rootstock tree that exhibits desirable disease resistance and induces a high yield of large fruits for grafted varieties.

4 Drawing Sheets

Botanical classification: *Prunus domestica* x *Prunus spinosa.*

Varietal denomination: 'Dhprs2'.

BACKGROUND OF THE INVENTION

The present invention comprises a new and distinct cultivar of (*Prunus domestica* x *Prunus spinosa*) used as a rootstock and known by the varietal name 'Dhprs2'. The new variety is the result of a planned breeding program conducted in Freising, Germany. The new variety is the result of a cross between *Prunus domestica* variety named 'Jojo' (female parent, unpatented) and an unnamed *Prunus spinosa* variety (male parent, unpatented). The new variety was first asexually reproduced via in vitro propagation using buds of one year old shoots of the original seedling plant in Freising, Germany.

'Dhprs2' has a similar one year old shoot color to 'Jojo'. However, the new variety exhibits a smaller fruit size and flowers five days earlier than 'Jojo'. Further, 'Dhprs2' has a similar leaf color to its male parent. However, the new variety exhibits larger leaves, larger fruits, and greater thickness of one year old shoots when compared to its male parent.

When compared to *Prunus domestica* variety named 'Wangenheims' (unpatented), 'Dhprs2' exhibits smaller fruits with a later ripening time. Further, the leaves of 'Wangenheims' are more bright green in color versus the dark green color 'Dhprs2' and the color of one year old shoots in August of 'Wangenheims' is greenish-brown versus the brown-violet color of 'Dhprs2'.

The new variety has not been evaluated under all possible environmental conditions. The phenotype may vary with variations in environment without a change in the genotype of the plant. The new variety has been trial and field tested and has been found to retain its distinctive characteristics and remain true to type through successive asexual propagations.

DESCRIPTION OF THE DRAWINGS

The accompanying photographic drawings illustrate the new variety at approximately 4 years of age, with the color being as nearly true as possible with color illustrations of this type.

DETAILED BOTANICAL DESCRIPTION

Figure 1:
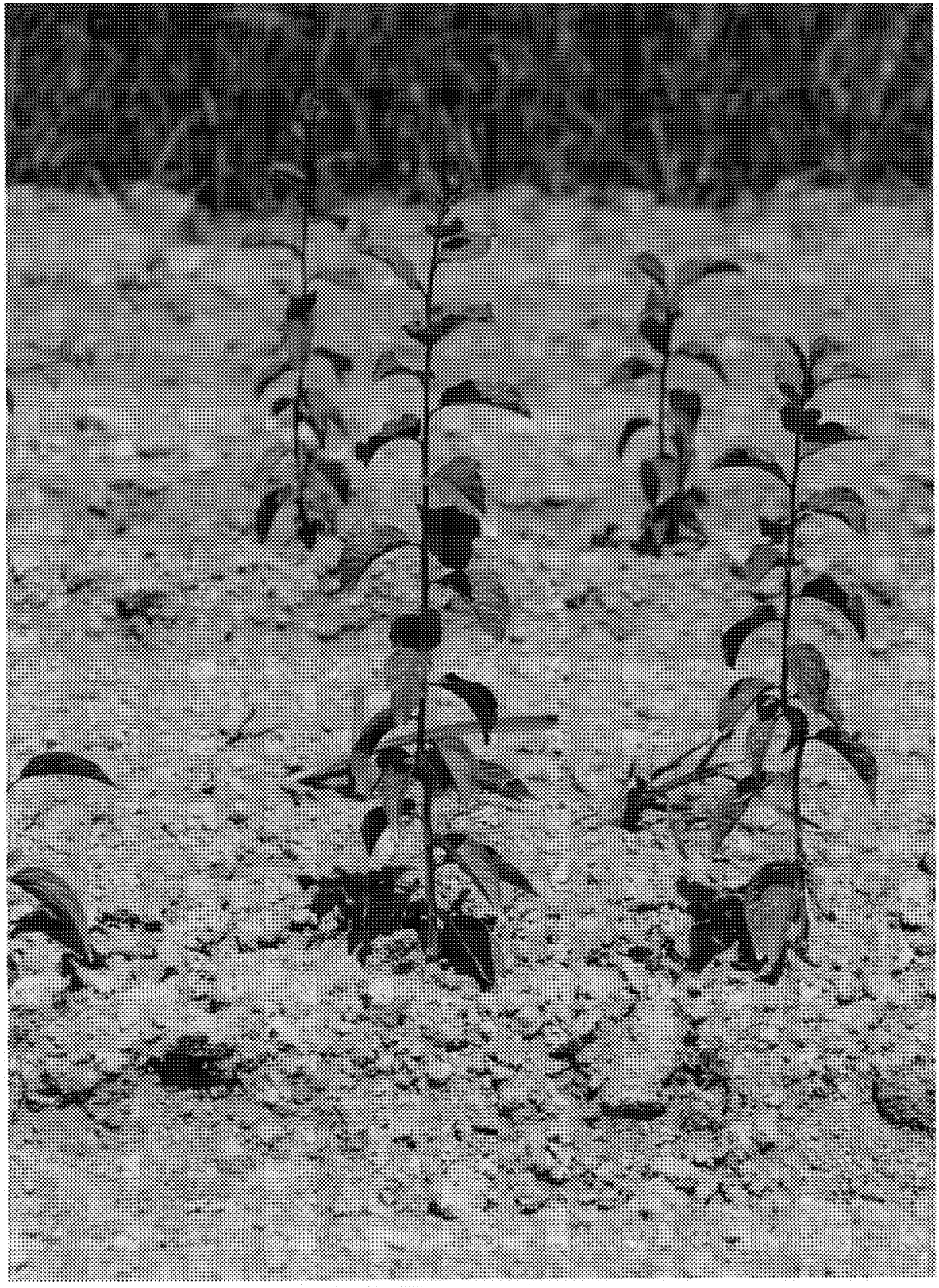
FIG. 1 illustrates numerous plants of 'Dhprs2'.
Figure 2:
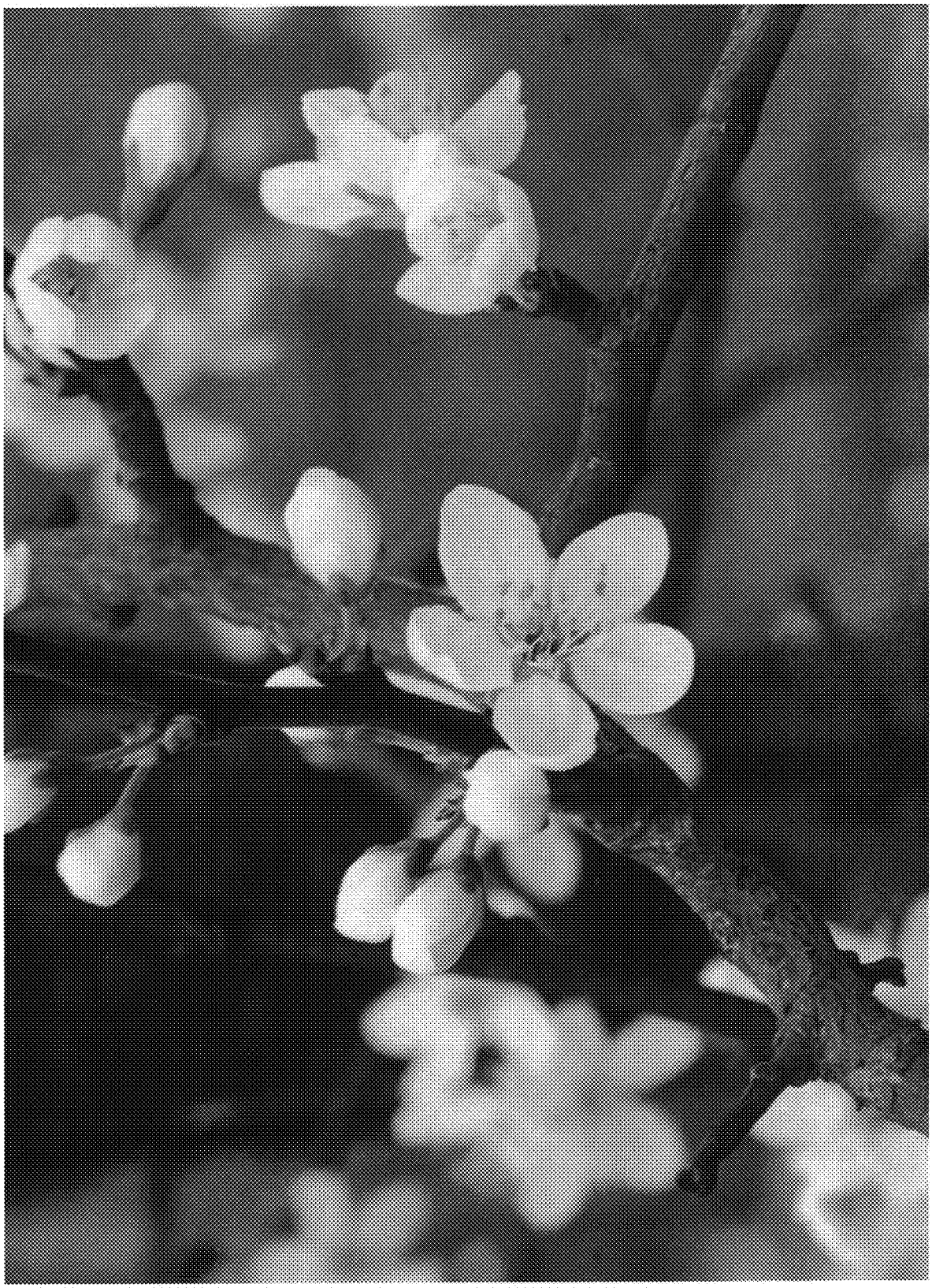
FIG. 2 illustrates the flowers of 'Dhprs2'.
Figure 3:
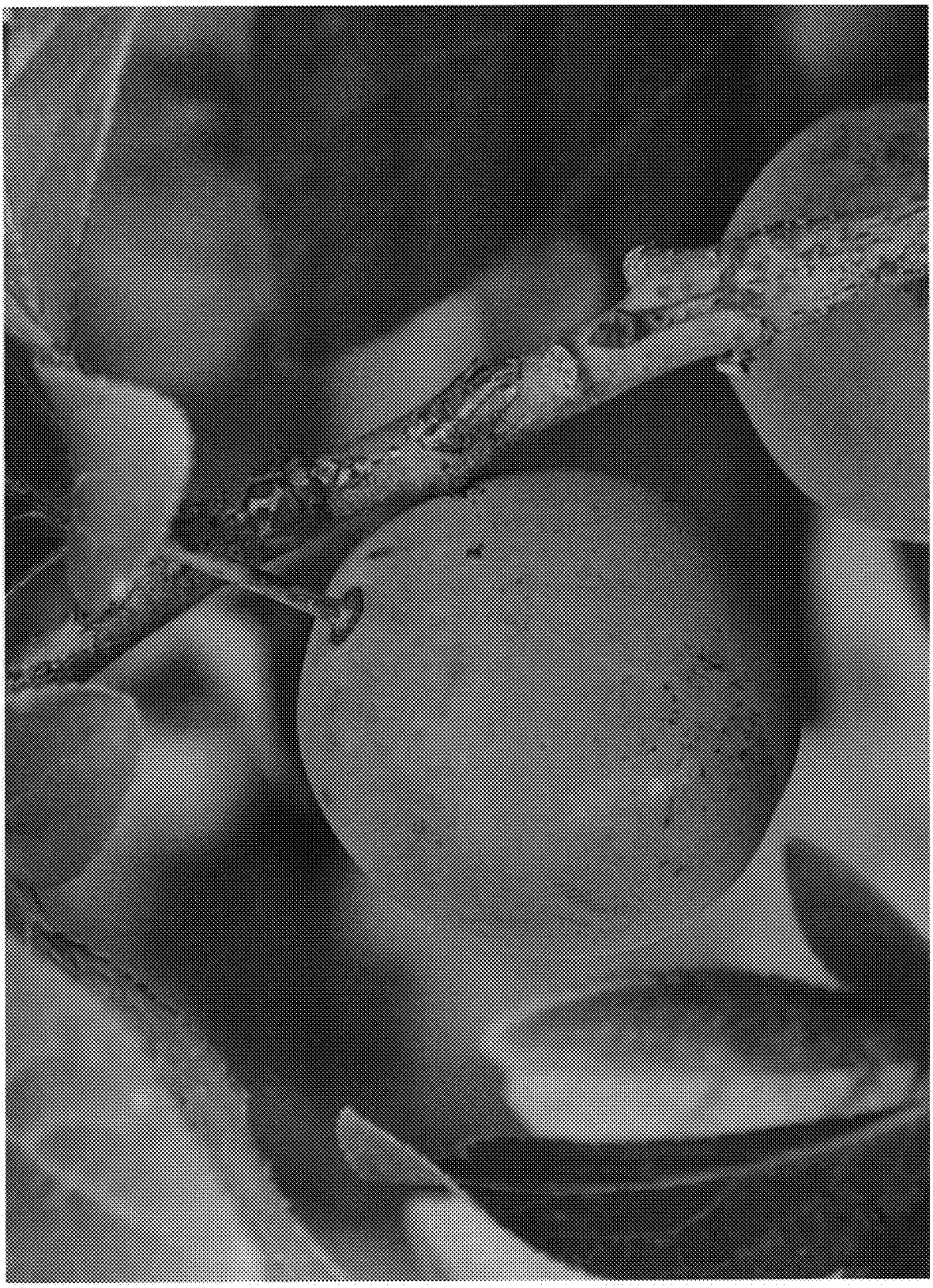
FIG. 3 illustrates the fruit of 'Dhprs2'.
Figure 4:
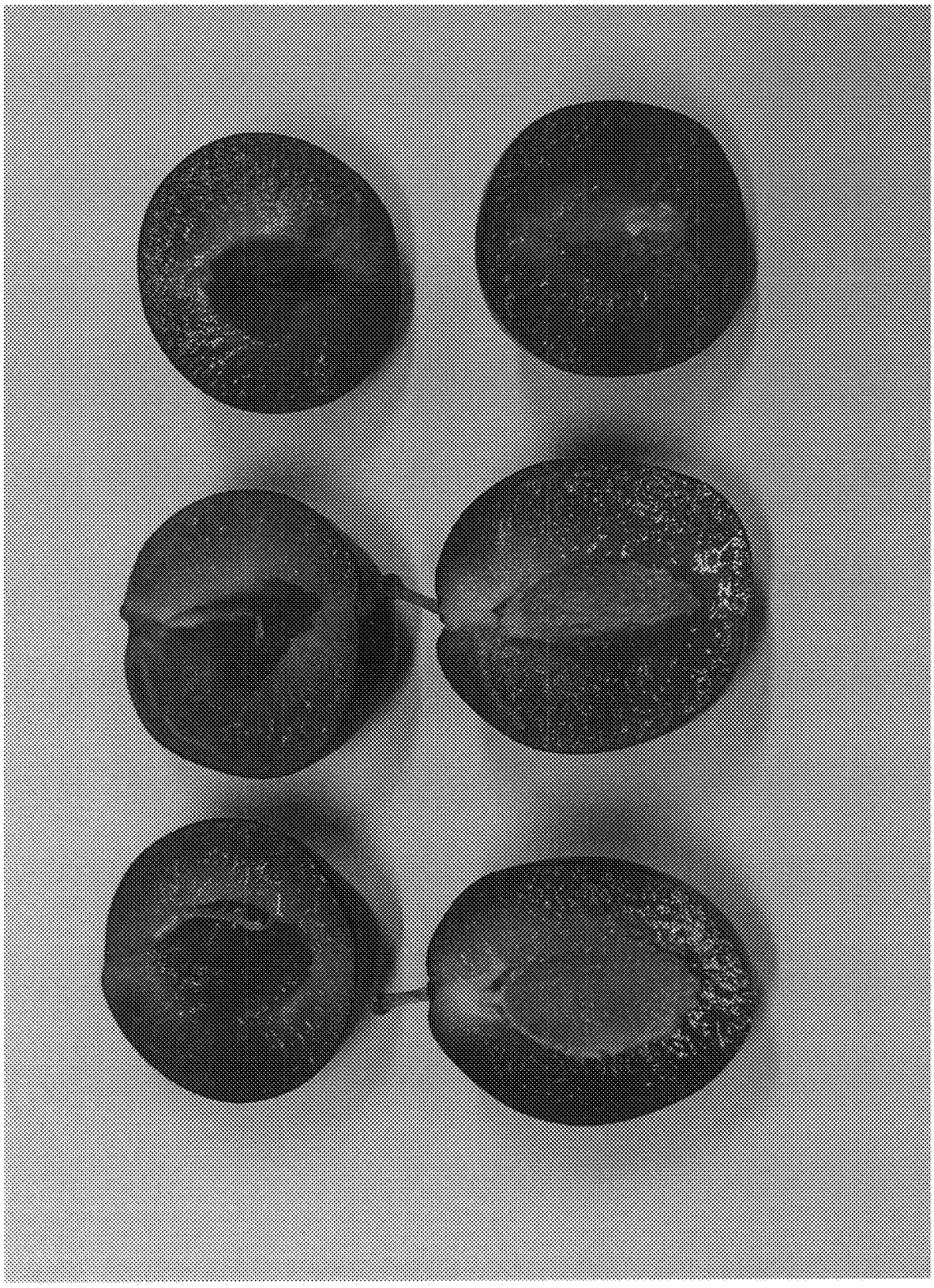
FIG. 4 illustrates sliced fruit of 'Dhprs2'.

The following detailed description sets forth the characteristics of the new cultivar at approximately 6 years of age.

The data which defines these characteristics were collected as a result of asexual reproductions carried out in Freising, Germany. 'Dhprs2' is compatible with at least varieties of *Prunus domestica* and *Prunus salicina* and induces a high yield of large fruits for grafted varieties. 'Dhprs2' is fully resistant to the Plum pox virus (PPV/Sharka) by means of hypersensitivity resistance. Further, the new variety exhibits good resistance to plum decline caused by *Pseudomonas* bacteria. 'Dhprs2' exhibits medium vigor (similar to *Prunus* rootstock variety named 'Weiwa'—unpatented) with only a few suckers present. Its leaf blades are narrow, serrate, elliptical in shape, and of medium length. Its flower petals are pure white in color. 'Dhprs2' can be useful as a rootstock for grafting of PPV resistant varieties, as well as with varieties that are PPV sensitive. Color references are primarily to The R.H.S. Colour Chart of The Royal Horticultural Society of London and were identified under natural light.

Rootstock:

Size: Medium.

Vigor: Moderate.

Tree habit: Spreading.

Pathogen resistance: Resistant to the Plum pox virus (PPV/Sharka) and good resistance to *Pseudomonas* bacteria.

Rootstock performance:

*Root sprouts* (*suckering*).—Few.

*Anchorage*.—Good.

*Compatibility*.—Very good with *Prunus domestica*; also compatible with *Prunus salicina*.

*Vigor*.—Moderate (70% with *Prunus cerasifera*).

Bearing: Regular.

Type of bearing: On spurs and long shoots, but mostly on spurs.

Trunk:

*Length*.—60.0 cm.

*Width*.—60.0 mm (measured at 30.0 cm from ground level).

*Lenticels*.—Length: Average of 3.0 mm. Width: Average of 0.8 mm. Number: Average of 3.2 per square centimeter.

Branches:

*One year old shoot color*.—Brown-violet.

*Diameter*.—Average of 12.0-15.0 mm.

*Color*.—RHS N200C.

*Lenticels*.—Length: 0.9-1.2 mm. Width: 0.1-0.2 mm. Number: Average of 1.8 per square millimeter. Color: RHS N199C.

Leaves:

*Length*.—64-70 mm.

*Width*.—42-49 mm.

*Form*.—Elliptic.

*Base*.—Obtuse-truncate.

*Apex*.—Apiculate.

*Margin*.—Crenate-serrate.

*Mature leaf color*.—Upper surface: RHS 137A. Lower surface: RHS 137C.

*Petiole*.—Length: 11-14 mm. Diameter: 1.5-1.8 mm. Color: RHS N77A.

*Veins*.—Venation type: Reticulate. Color: RHS 141D.

Vegetative buds:

*Spur length*.—Average of 32.0 mm.

*Bud length*.—Average of 1.5 mm.

*Bud diameter*.—Average of 0.4 mm.

Flowers:

*Bud length*.—Average of 1.9 mm.

*Bud diameter*.—Average of 0.8 mm.

Fruit:

*Ripening time*.—Begins in the middle of September in Freising, Germany.

*Bloom on skin*.—Present.

*Area of fruit over color*.—100%.

*Skin color*.—RHS 202A.

*Flesh color*.—RHS 152B.

*Stalk length*.—6.5-9.8 mm.

*Stalk color*.—RHS 145A.

*Symmetry*.—Slightly asymmetric.

*Base*.—Slightly depressed.

*Apex*.—Slightly depressed.

*Depth of stalk cavity*.—0.5 mm.

*Lenticels*.—Average of 2 per square millimeter.

*Lenticel size*.—Less than 0.5 mm.

*Fruit firmness*.—Medium.

*Sweetness*.—15-17 Brix.

*Stone*.—Adherence: Little to no adherence to flesh. Length: 20.4-20.8 mm. Breadth: 12.0-12.6 mm. Thickness: 7.4-7.8 mm. Shape in lateral view: Narrow elliptic to elliptic. Shape in ventral view: Elliptic. Shape in basal view: Elliptic. Texture of lateral surfaces: Hammered. Width of stalk end: Very narrow.

Tree winter hardiness: High.

Bud winter hardiness: High.

Drought tolerance: Good.

I claim:

1. A new and distinct variety of *Prunus* rootstock plant, as illustrated and described herein.

* * * * *